(12) United States Patent
Tada et al.

(10) Patent No.: US 12,369,941 B2
(45) Date of Patent: Jul. 29, 2025

(54) MEDICAL DEVICE

(71) Applicant: TERUMO KABUSHIKI KAISHA, Tokyo (JP)

(72) Inventors: Yuichi Tada, Santa Clara, CA (US); John Barritt, San Jose, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 522 days.

(21) Appl. No.: 17/685,323

(22) Filed: Mar. 2, 2022

(65) Prior Publication Data

US 2022/0183715 A1   Jun. 16, 2022

Related U.S. Application Data

(63) Continuation of application No. PCT/JP2020/030840, filed on Aug. 14, 2020.

(30) Foreign Application Priority Data

Sep. 4, 2019  (JP) ................................ 2019-160859

(51) Int. Cl.
*A61B 17/3207* (2006.01)

(52) U.S. Cl.
CPC .. *A61B 17/320758* (2013.01); *A61B 17/3207* (2013.01); *A61B 2217/005* (2013.01)

(58) Field of Classification Search
CPC ........ A61B 17/3207; A61B 17/320758; A61B 2217/005; A61B 17/320016; A61B 17/32002; A61B 17/320024; A61B 17/320725; A61B 2017/320024; A61B 2017/320028; A61B 2017/320032; A61B 2017/320716

See application file for complete search history.

(56) References Cited

U.S. PATENT DOCUMENTS

| 4,274,414 A | 6/1981 | Johnson et al. |
| 4,857,045 A | 8/1989 | Rydell |
| 2003/0083684 A1* | 5/2003 | Cesarini ........... A61B 17/32002 606/171 |

(Continued)

FOREIGN PATENT DOCUMENTS

| JP | S55-116346 A | 9/1980 |
| JP | H01-115352 A | 5/1989 |

(Continued)

*Primary Examiner* — Kelly J Bekker
*Assistant Examiner* — Lindsey R. Rivers
(74) *Attorney, Agent, or Firm* — Kim & Stewart LLP (57) ABSTRACT

A medical device that removes an object from a biological lumen, includes a rotatable drive shaft having a lumen through which the object passes, a cutting unit disposed at a distal end of the drive shaft and by which the object is cut, a proximal shaft to be rotated by a rotary force, a connection unit connecting the proximal shaft and the drive shaft and by which the rotary force is transmitted to the drive shaft, and a housing that houses the connection unit and includes a discharge port communicating with the lumen via the connection unit and through which the cut object is discharged. The connection unit includes a surface that faces a proximal end of the drive shaft and prevents the object that passed through the lumen and is to be discharged from being retained in the connection unit along a rotation axis thereof.

11 Claims, 5 Drawing Sheets

(56) References Cited

U.S. PATENT DOCUMENTS

| | | | |
|---|---|---|---|
| 2009/0024085 A1* | 1/2009 | To | A61B 17/320758 |
| | | | 604/95.01 |
| 2009/0234378 A1* | 9/2009 | Escudero | A61M 25/09 |
| | | | 606/159 |
| 2018/0055535 A1* | 3/2018 | Tada | A61M 25/0023 |
| 2018/0271544 A1* | 9/2018 | Magno | A61B 17/1644 |
| 2018/0353199 A1 | 12/2018 | Tada et al. | |

FOREIGN PATENT DOCUMENTS

| | | |
|---|---|---|
| JP | H05-31117 A | 2/1993 |
| JP | 2011-517601 A | 6/2011 |

* cited by examiner

MEDICAL DEVICE

CROSS-REFERENCE TO RELATED APPLICATION(S)

This application is a continuation of International Patent Application No. PCT/JP2020/030840 filed Aug. 14, 2020, which is based upon and claims the benefit of priority from Japanese Patent Application No. 2019-160859 filed Sep. 4, 2019, the entire contents of which are incorporated herein by reference.

BACKGROUND OF THE INVENTION

Field of the Invention

Embodiments described herein generally relate to a medical device for removing an object from a biological lumen.
Background Art
Examples of a treatment method for a stenosis site caused by a plaque, a thrombus, and the like in a blood vessel include a method of dilating the blood vessel by using a balloon, a method of indwelling a mesh-shaped or coil-shaped stent in the blood vessel as a support for the blood vessel, and the like. However, it is difficult for these methods to treat a stenosis site that is hardened by calcification or a stenosis site that is formed at a branched portion of the blood vessel. A method capable of performing treatment in such a case includes a method of cutting and removing a stenotic object such as a plaque or a thrombus.

For example, there is a known device in which an operation head for cutting an object is fixed to a distal section of a drive shaft. The device can rotate the drive shaft to cut the object with the operation head. The device includes, on the operator or proximal side, a housing provided with a discharge port that applies an aspiration force. Debris formed by cutting is aspirated from a distal opening portion of the drive shaft into a lumen and is moved to the proximal side. Then, the debris moves into the housing from a proximal opening portion of the drive shaft and is discharged from the discharge port.

The debris may easily wind around the rotating drive shaft in the housing. When the debris blocks an opening portion on the proximal side of the drive shaft, the debris is retained in the housing and is difficult to be discharged from the discharge port to an outside.

SUMMARY OF THE INVENTION

According to one embodiment, a medical device that removes an object from a biological lumen, includes a rotatable drive shaft having a lumen through which the object passes, a cutting unit disposed at a distal end of the drive shaft and by which the object is cut, a proximal shaft to be rotated by a rotary force, a connection unit connecting the proximal shaft and the drive shaft and by which the rotary force is transmitted to the drive shaft, and a housing that houses the connection unit and includes a discharge port communicating with the lumen via the connection unit and through which the cut object is discharged. The connection unit includes a surface that faces a proximal end of the drive shaft and prevents the object that has passed through the lumen and is to be discharged through the discharged port from being retained in the connection unit along a rotation axis thereof.

In another embodiment, a medical device that removes an object from a biological lumen, includes a rotatable drive shaft having a lumen through which the object passes, a proximal shaft to be rotated by a rotary force, a connection unit connecting the proximal shaft and the drive shaft and by which the rotary force is transmitted to the drive shaft, and a housing that houses the connection unit and includes a discharge port communicating with the lumen via the connection unit and through which the object is discharged. The connection unit includes a surface that faces a proximal end of the drive shaft and prevents the object that has passed through the lumen and is to be discharged through the discharged port from being retained in the connection unit along a rotation axis thereof.

In yet another embodiment, a medical device that removes an object from a biological lumen, includes a rotatable drive shaft having a lumen through which the object passes, a cutting unit disposed at a distal end of the drive shaft and by which the object is cut, a drive device configured to generate a rotary force, a proximal shaft to be rotated by the rotary force, a connection unit connecting the proximal shaft and the drive shaft and by which the rotary force is transmitted to the drive shaft, and a housing that houses the connection unit and includes a discharge port communicating with the lumen via the connection unit and through which the cut object is discharged. The connection unit includes a surface that faces a proximal end of the drive shaft and prevents the object that has passed through the lumen and is to be discharged through the discharged port from being retained in the connection unit along a rotation axis thereof.

In the medical devices configured as described above, it is difficult for the object flowing to the proximal side through the lumen of the drive shaft to wind around the rotation axis of the connection unit. Thus, the opening portion on the proximal side of the drive shaft is prevented from being completely blocked by the object. Therefore, the medical device is capable of aspirating the object in the biological lumen to prevent the object from being retained in the device, and effectively discharging the object.

DESCRIPTION OF EMBODIMENTS

Hereinafter, embodiments of the invention will be described with reference to drawings. Note that a size or ratio of each member in the drawings may be exaggerated for convenience of description and may differ from an actual size or ratio.

First Embodiment

A medical device 10 according to a first embodiment is inserted into a blood vessel in an acute lower limb ischemia or a deep vein thrombosis, and is used in a treatment to destroy and remove an object such as a thrombus, plaque, an atheroma, or a calcified lesion. In the present specification, a side of the medical device 10 which is inserted into the blood vessel is referred to as a "distal side", and an operating hand side is referred to as a "proximal side". An object to be removed is not necessarily limited to the thrombus, the plaque, the atheroma, or the calcified lesion, and may be any object that may exist in a biological lumen.

Figure 1:
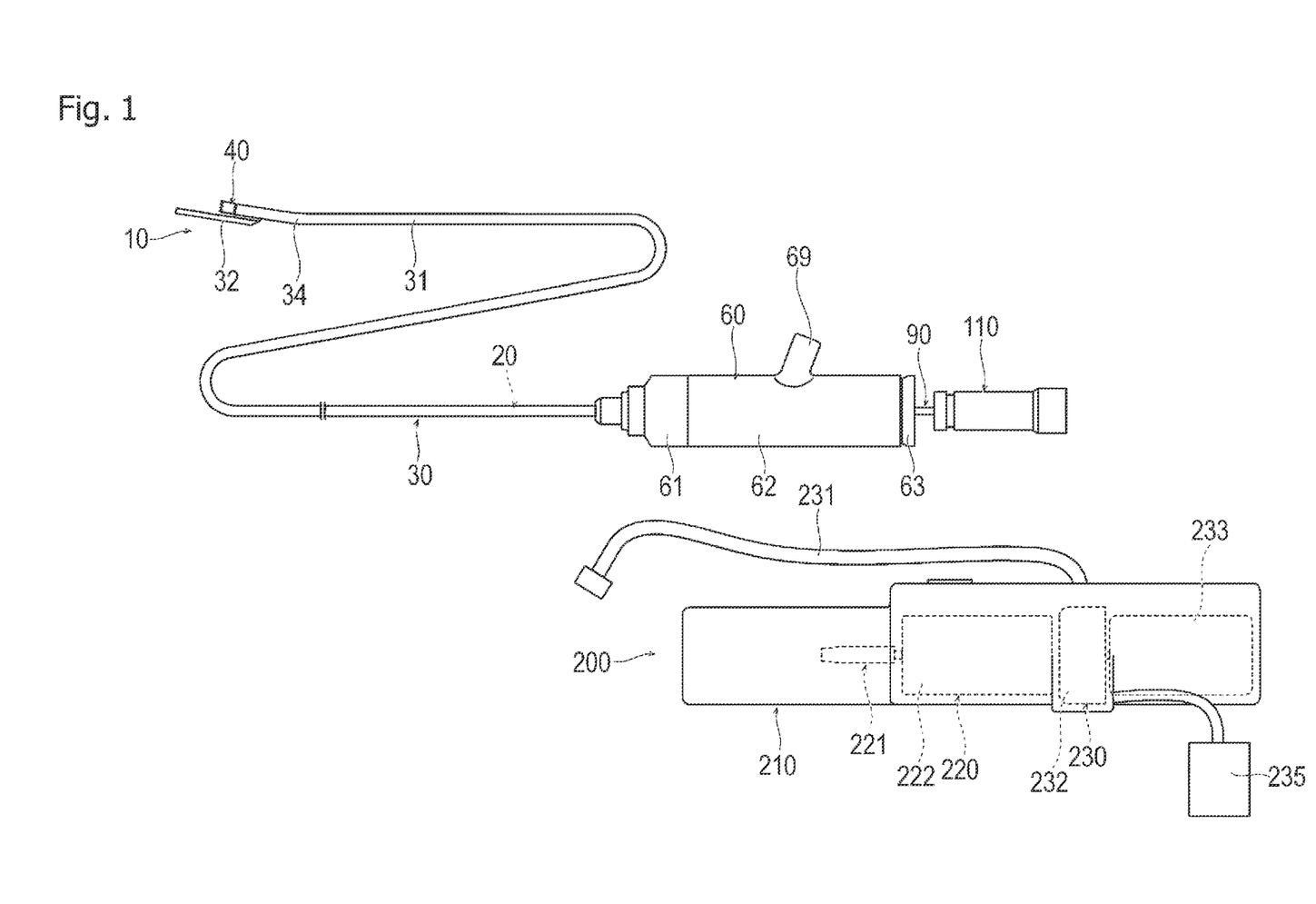
FIG. 1 is a plan view showing a medical device and a drive device according to a first embodiment.
Figure 2:
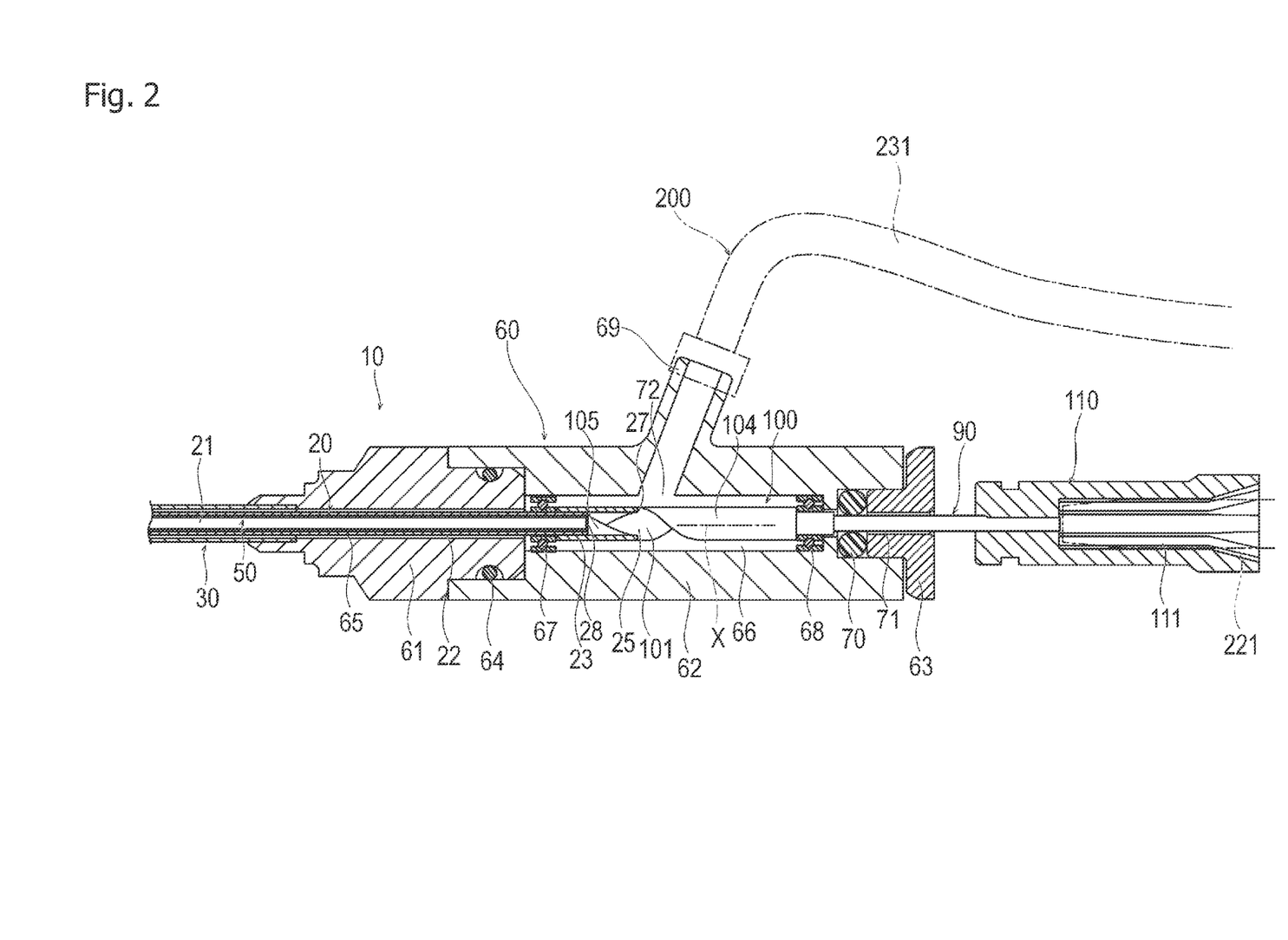
FIG. 2 is a cross-sectional view showing a proximal section of a medical device according to a first embodiment.

As shown in FIGS. 1 and 2, the medical device 10 is connected to and driven by a drive device 200 that generates a drive force and an aspiration force. The medical device 10 includes an elongated drive shaft 20 that is rotationally driven, an outer tube 30 that accommodates the drive shaft 20, and a cutting unit 40 that cuts the object. The medical device 10 further includes an inner tube 50 that is disposed inside the drive shaft 20, a proximal shaft 90 that is disposed on a proximal side of the drive shaft 20, and a connection unit 100 that connects the proximal shaft 90 and the drive shaft 20. The medical device 10 further includes a housing 60 that rotatably holds a proximal section of the drive shaft 20 and a rotary input unit 110 that receives a rotary force from the drive device 200.

The drive shaft 20 transmits the rotary force to the cutting unit 40. The drive shaft 20 includes an aspiration lumen 21 for moving the cut object to the proximal side. The drive shaft 20 includes an elongated drive shaft body 22 and an auxiliary member 23 fixed to a proximal section of the drive shaft body 22. The drive shaft 20 penetrates the outer tube 30, and the cutting unit 40 is fixed on a distal section thereof. The proximal section of the drive shaft 20 is located inside the housing 60. The drive shaft 20 is connected to the proximal shaft 90 via the connection unit 100. The drive shaft 20 has, on the distal end thereof, a distal opening portion 26 (see FIG. 4) through which the aspiration lumen 21 opens. The distal opening portion 26 is an inlet for debris which is an aspiration object formed by cutting. The drive shaft 20 has a proximal opening portion 25 on the proximal end thereof. The proximal opening portion 25 is an outlet from which the debris that has entered the drive shaft 20 from the distal opening portion 26 is released. The proximal opening portion 25 opens toward the proximal side.

The drive shaft body 22 is flexible and has a characteristic in which rotational power applied from the proximal side can be transmitted to the distal side. The drive shaft body 22 is rotatably supported inside the housing 60 by a first bearing 67 which will be described later. Therefore, the drive shaft body 22 can rotate smoothly at a high speed.

The auxiliary member 23 is tubular, and the proximal section of the drive shaft body 22 is inserted into the auxiliary member 23 from an opening at the distal side thereof. The connection unit 100 is inserted into the auxiliary member 23 from an opening at the proximal side thereof. An inner diameter of the auxiliary member 23 is substantially the same as an outer diameter of the drive shaft body 22. Thus, the drive shaft body 22 fits inside the auxiliary member 23. Therefore, the drive shaft body 22 and the auxiliary member 23 are stably connected. A proximal end face 27 of the auxiliary member 23 is a proximal end face of the drive shaft 20 and is ring-shaped. The proximal end face 27 of the auxiliary member 23 is the most proximal side of the auxiliary member 23 and faces the axial direction thereof. The drive shaft body 22 may be connected to the connection unit 100 without the auxiliary member 23. That is, the drive shaft 20 is configured with the drive shaft body 22 and may not include the auxiliary member 23.

The rotary input unit 110 that receives a rotary force from the drive device 200 is fixed to a proximal section of the proximal shaft 90. The proximal section of the proximal shaft 90 projects from the housing 60 to the proximal side. The proximal shaft 90 is rotatably supported inside the housing 60 by a second bearing 68 which will be described later. Thus, the proximal shaft 90 can rotate smoothly at a high speed.

Figure 3A:
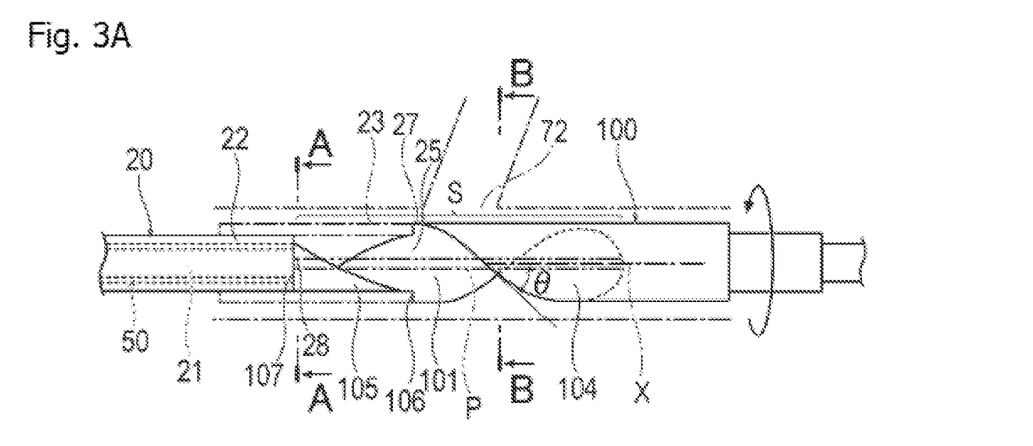
FIG. 3A is a diagram showing a partially transparent view of the vicinity of a connection unit of a medical device according to a first embodiment.
Figure 3B:
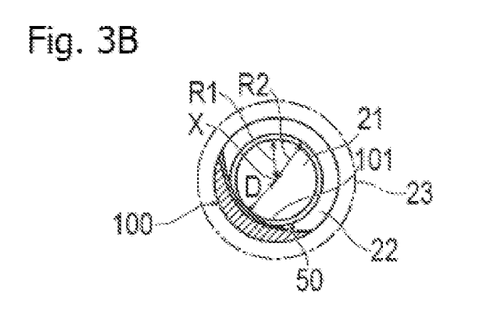
FIG. 3B is a cross-sectional view taken along a line A-A of FIG. 3A
Figure 3C:
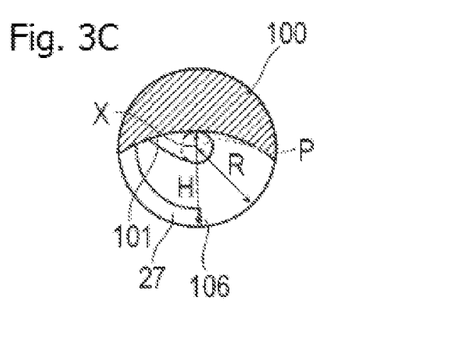
FIG. 3C is a cross-sectional view taken along a line B-B of FIG. 3A.

As shown in FIGS. 2 and 3, the connection unit 100 is a member that connects the drive shaft 20 at the distal side and the proximal shaft 90 at the proximal side. The connection unit 100 is connected to the drive shaft 20 without blocking the proximal opening portion 25, that opens toward the proximal side, of the drive shaft 20. The connection unit 100 extends from the connected drive shaft 20 to the proximal side. In the present embodiment, the connection unit 100 is integrally formed with the proximal shaft 90, but may be formed separately from the proximal shaft 90.

The connection unit 100 is a substantially cylindrical shape, and one spiral groove 101 is formed on an outer peripheral surface of the connection unit 100. The connection unit 100 includes a spiral proximal section 104 located on the proximal side and having a large outer diameter and a spiral distal section 105 located on a distal side of the spiral proximal section 104 and having a smaller outer diameter than that of the spiral proximal section 104.

As shown in FIG. 3A, a step unit 106 whose outer diameter changes stepwise is formed between the spiral distal section 105 and the spiral proximal section 104. The step unit 106 abuts on the proximal end face 27 of the drive shaft 20. A shape of an end face of the step unit 106, that abuts on the proximal end face 27 of the drive shaft 20, of the connection unit 100 is different from that of the proximal end face 27 of the drive shaft 20. A cross-sectional shape of the connection unit 100 on a plane where the proximal end face 27 of the drive shaft 20 is located is different from a shape of the proximal end face 27. Thus, the connection unit 100 can be fixed to the proximal section of the drive shaft 20 without blocking the opening facing the axial direction of the proximal opening portion 25 of the drive shaft 20. The plane where the proximal end face 27 of the drive shaft 20 is located is preferably a flat plane, but may not be a flat plane, and may be, for example, a curved plane or a bent plane.

The connection unit 100 may have a constant outer diameter without being divided into the spiral proximal section 104 and the spiral distal section 105. For example, the connection unit 100 may have an outer diameter that enables the connection unit 100 to enter the proximal opening portion 25 without being provided with the step unit 106. In this case, the connection unit 100 enters the proximal opening portion 25 and is fixed to the drive shaft 20 without the step unit 106 abutting on the proximal end face 27.

A distal end face 107 of the spiral distal section 105 abuts on a proximal end face 28 of the drive shaft body 22 inside the auxiliary member 23. The distal end face 107 of the spiral distal section 105 does not have to abut on the proximal end face 28 of the drive shaft body 22.

The outer diameter of the spiral proximal section 104 is substantially equal to an outer diameter of the auxiliary member 23, but does not have to be equal. An outer diameter of the spiral distal section 105 is substantially equal to the inner diameter of the auxiliary member 23. Therefore, the spiral distal section 105 fits into a lumen of the auxiliary member 23, and the spiral distal section 105 is stably connected to the auxiliary member 23. The step unit 106 is in contact with the proximal end face 27 of the auxiliary member 23. Accordingly, the connection unit 100 and the auxiliary member 23 are stably connected in the axial direction.

The connection unit 100 is formed separately from the auxiliary member 23, but may be integrally formed with the auxiliary member 23. That is, the auxiliary member 23, which is a part of the drive shaft 20, may be integrally formed with the connection unit 100. In this case, a cylindrical shape including the proximal opening portion 25 can be specified as the auxiliary member 23. That is, the drive shaft 20 extends to a proximal end of a portion where an inner wall surface is formed over 360 degrees and which surrounds an internal space all around. The proximal opening portion 25 opens in the axial direction from the proximal end of the portion where the inner wall surface is formed over 360 degrees. Therefore, the proximal end face 28 of the auxiliary member 23 may be located inside the integrally formed member.

When the drive shaft 20 does not include the auxiliary member 23, the proximal end face of the drive shaft 20 is the proximal end face 28 of the drive shaft body 22 and is ring-shaped. The cross-sectional shape of the connection unit 100 (i.e., the shape of the distal end face 107) on a plane where the proximal end face 28 of the drive shaft body 22 is located is different from the shape of the proximal end face 28.

The spiral groove 101 is spirally formed on the outer peripheral surface of the connection unit 100 from the distal end face 107 toward the proximal side of the connection unit 100. The spiral groove 101 communicates with the aspiration lumen 21 of the drive shaft 20 at the distal end face 107 of the connection unit 100. The spiral groove 101 does not have to be formed up to the proximal end face of the connection unit 100, but may be formed up to the proximal end face.

A spiral direction of the spiral groove 101 is a direction in which the object inside the spiral groove 101 receives a force toward the proximal side when the connection unit 100 is rotated by the rotary force transmitted from the drive device 200. For example, when looking from the proximal side to the distal side, if a rotation direction of the connection unit 100 is clockwise, a winding direction of the spiral groove 101 of the connection unit 100 is clockwise toward the distal side. When looking from the proximal side to the distal side, if the rotation direction of the connection unit 100 is counterclockwise, the winding direction of the spiral groove 101 of the connection unit 100 is counterclockwise toward the distal side. A depth H of the spiral groove 101 from the outer peripheral surface toward a central axis X of the connection unit 100 is not particularly limited, but may be larger than, for example, a distance R from the outer peripheral surface to the central axis X of the connection unit 100. Accordingly, in a cross section orthogonal to the central axis X (hereinafter referred to as "axis orthogonal cross section") of the connection unit 100, a central path P (see a two-dot chain line in FIG. 3A) extending linearly along the central axis X of the connection unit 100 is formed. That is, the central path P surrounding the central axis X is formed at a center of the connection unit 100, and a material of the connection unit 100 does not exist on the central axis X. Therefore, the aspiration lumen 21 of the drive shaft 20 and the central path P of the connection unit 100 communicate linearly with each other along the central axis X. The depth H of the spiral groove 101 may be equal to or less than the distance R of the connection unit 100.

A spiral angle θ of the spiral groove 101 with respect to the central axis X is not particularly limited, but is, for example, 1 to 89 degrees, preferably 10 to 60 degrees, and more preferably 20 to 50 degrees. If the angle θ is too close to 90 degrees, it will be difficult for the debris to pass through the spiral groove 101. If the angle θ is too close to 0 degrees, the rotating spiral groove 101 weakens a force that transports the debris to the proximal side. The spiral angle θ may change along the central axis X of the connection unit 100. For example, the spiral angle θ may be closer to 0 degrees on a distal side of the connection unit 100 and closer to 90 degrees toward a proximal side. Accordingly, the spiral groove 101 can cause the debris to smoothly move.

A constituent material of the drive shaft body 22 is not particularly limited, and may preferably use, for example, stainless steel, Ta, Ti, Pt, Au, W, polyolefins such as polyethylene and polypropylene, polyesters such as polyamide and polyethylene terephthalate, fluoropolymers such as ETFE, polyetheretherketone (PEEK), polyimide, or the like. The constituent material may be composed of a plurality of materials, and may be embedded with a reinforcing member such as a wire rod.

Constituent materials of the auxiliary member 23, the connection unit 100, and the proximal shaft 90 are not particularly limited, and may preferably use, for example, stainless steel, Ta, Ti, Pt, Au, W, and shape memory alloy. The constituent materials of the auxiliary member 23, the connection unit 100, and the proximal shaft 90 may be a resin such as engineering plastic such as polyetheretherketone (PEEK).

As shown in FIG. 2, the rotary input unit 110 is a substantially cylindrical member fixed to the proximal end of the drive shaft 20. The rotary input unit 110 is a member that is connected to a rotation drive shaft 221 of the drive device 200 to receive the rotational power. A proximal section of the rotary input unit 110 includes a fitting recessed portion 111 into which the rotation drive shaft 221 is fitted.

Figure 4:
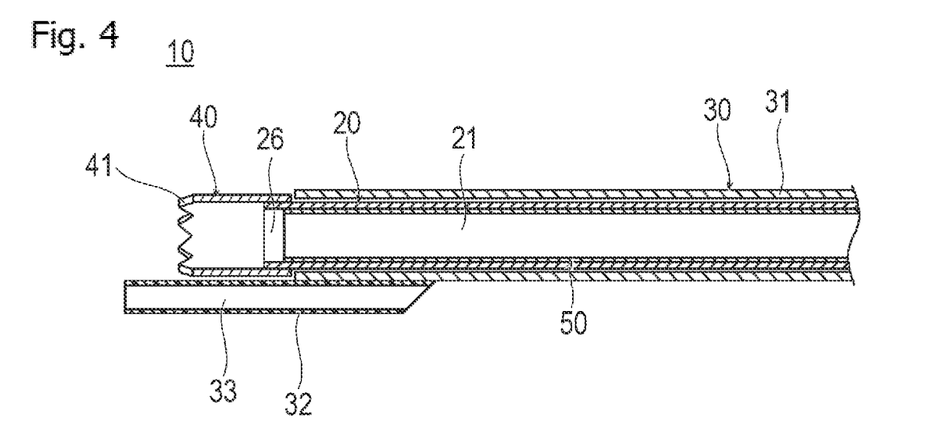
FIG. 4 is a cross-sectional view showing a distal section of a medical device according to a first embodiment.

As shown in FIGS. 2 and 4, the inner tube 50 is a flexible tube body and is disposed inside the drive shaft 20. The inner tube 50 prevents damage to an inner peripheral surface of the drive shaft 20 due to the debris flowing inside the drive shaft 20. The inner tube 50 may or may not be fixed on the inner peripheral surface of the drive shaft 20. As shown in FIG. 3B, a radius R1 of an inner peripheral surface of the inner tube 50 is smaller than a distance D from the central axis X to a nearest portion of the connection unit 100 at the distal end face 107 of the connection unit 100. The distance D is smaller than a radius R2 of an inner peripheral surface of the drive shaft body 22. Thus, a part of the distal end face 107 of the connection unit 100 is located at an inner side in a diameter direction of the inner peripheral surface of the drive shaft body 22. Therefore, as the inner tube 50 moves in the aspiration lumen 21 to the proximal side, the proximal end face of the inner tube 50 comes into contact with the distal end face 107 of the connection unit 100. Thus, the inner tube 50 is prevented from entering the spiral groove 101 of the connection unit 100.

In one embodiment, the inner tube 50 may be omitted and may not be provided inside the drive shaft 20.

As shown in FIGS. 1, 2, and 4, the outer tube 30 includes an outer tube body 31 that rotatably accommodates the drive shaft 20 and a distal tube 32 that is fixed on a side surface of a distal section of the outer tube body 31.

The outer tube body 31 is a flexible tube body, and a proximal section of the outer tube body 31 is fixed to the housing 60. The distal section of the outer tube body 31 is located at a proximal side of the cutting unit 40. A distal tube 32 is a flexible tube body and is fixed on an outer peripheral surface of the distal section of the outer tube body 31. The distal tube 32 has a guide wire lumen 33 into which a guide wire can be inserted.

As shown in FIGS. 1 and 4, the cutting unit 40 is a member that cuts and reduces an object such as a thrombus, a plaque, or a calcified lesion. Therefore, the "cutting" means applying a force to a contact object to remove or make the object smaller. A method of applying a force in the cutting, and a shape or a form of the object after the cutting are not limited. The cutting unit 40 is capable of applying a force enough to cut the above-described object. The cutting unit 40 is fixed on an outer peripheral surface of the distal section of the drive shaft 20. The proximal end face of the cutting unit 40 may be fixed on a distal end face of the drive shaft 20. The cutting unit 40 is a cylinder protruding to a distal side of the drive shaft 20. A distal end of the cutting unit 40 includes a sharp blade 41. A shape of the blade 41 is not particularly limited. The cutting unit 40 may have a large number of fine abrasive grains instead of the blade 41.

As shown in FIGS. 1 and 2, the housing 60 includes a first portion 61 disposed at a distal side, a second portion 62 disposed approximately in the center, and a third portion 63 disposed at a proximal side.

The first portion 61 is connected to a distal section of the second portion 62. A first sealing portion 64 that seals an internal space is disposed between the first portion 61 and the second portion 62. The first portion includes a first internal space 65 through which the drive shaft 20 rotatably penetrates. The proximal section of the outer tube body 31 is fixed on an inner peripheral surface at a distal side of the first internal space 65.

The second portion 62 is located at a proximal side of the first portion 61. The second portion 62 includes a second internal space 66 through which the drive shaft 20, the connection unit 100, and the proximal shaft 90 rotatably penetrate. The second portion 62 has a discharge port 69 to which an aspiration tube 231 of the drive device 200 described later can be connected. A flow path of the discharge port 69 communicates with the second internal space 66. Along an inner peripheral surface of the second internal space 66, a first bearing 67 and a second bearing 68 are disposed. An inner peripheral surface of the first bearing 67 is in contact with the outer peripheral surface of the proximal section of the drive shaft 20. An inner peripheral surface of the second bearing 68 is in contact with an outer peripheral surface of a distal section of the proximal shaft 90. Thus, the drive shaft 20, the connection unit 100, and the proximal shaft 90 can be rotatably supported by the first bearing 67 and the second bearing 68 and can rotate smoothly at a high speed. Positions where the first bearing 67 and the second bearing 68 are disposed is not limited. For example, the first bearing 67 and/or the second bearing 68 may be fixed on the outer peripheral surface of the connection unit 100. The first bearing 67 and/or the second bearing 68 may not be provided.

The third portion 63 is connected to a proximal section of the second portion 62. The third portion 63 includes a third internal space 71 through which the proximal shaft 90 rotatably penetrates. A second sealing portion 70 that seals the second internal space 66 is disposed between the second portion 62 and the third portion 63. The second sealing portion 70 is in contact with the outer peripheral surface of the proximal shaft 90 and seals the gap between the second portion 62 and the proximal shaft 90.

The proximal opening portion 25 of the drive shaft 20 is located in the second internal space 66. Thus, a negative pressure applied to the discharge port 69 from the aspiration tube 231 is applied in the drive shaft 20 from the proximal opening portion 25. The first sealing portion 64 and the second sealing portion 70 prevent negative pressures of the first internal space 65 and the second internal space 66 from escaping. At least a part of a junction portion 72 where the flow path of the discharge port 69 connects to the second internal space 66 is preferably in a range S where the spiral groove 101 exists in the axial direction of the connection unit 100, as shown in FIG. 3A. The junction portion 72 is a portion where an inner surface forming the flow path of the discharge port 69 is connected to an inner surface forming the second internal space 66. The junction portion 72 is preferably close to the proximal opening portion 25. The junction portion 72 may partially overlap the proximal opening portion 25 in the axial direction of the connection unit 100. It is preferable that at least a part of the junction portion 72 is on a proximal side of the proximal opening portion 25 of the drive shaft 20 in the axial direction of the connection unit 100. A position of the junction portion 72 is not limited to the above range. A position of the proximal opening portion 25 of the drive shaft 20 is not particularly limited as long as the negative pressure from the discharge port 69 can be applied to this position.

Next, the drive device 200 will be described. As shown in FIG. 1, the drive device 200 includes a drive unit 220 generating the rotary force and an aspiration unit 230 generating the aspiration force.

The drive unit 220 includes the rotation drive shaft 221 and a first motor 222 that rotates the rotation drive shaft 221. A rotation speed of the first motor 222 is not particularly limited, but is, for example, 5,000 to 200,000 rpm.

The aspiration unit 230 includes an aspiration tube 231, a pump 232, a second motor 233, and a waste liquid pack 235. The aspiration tube 231 can be connected to the discharge port 69 of the medical device 10. The pump 232 is driven by the second motor 233 to apply a negative pressure to the aspiration tube 231. The pump 232 discharges a fluid aspirated through the aspiration tube 231 to the waste liquid pack 235.

A configuration of the drive device 200 is not limited to the above example. For example, a mechanism generating the rotary force and a mechanism generating the aspiration force may include separate devices.

Next, a method of using the medical device 10 according to the first embodiment will be described by taking, as an example, a case where a thrombus or a lesion such as a calcified lesion in a blood vessel is destroyed and aspirated.

First, a surgeon inserts a guide wire (not shown) into the blood vessel to reach the vicinity of the lesion. Next, the surgeon inserts a proximal end of the guide wire into the guide wire lumen 33 of the medical device 10. Then, the medical device 10 is brought to the vicinity of the lesion by using the guide wire as a guide.

Next, as shown in FIG. 2, the surgeon connects the rotation drive shaft 221 of the drive device 200 to the rotary input unit 110. Subsequently, the surgeon connects the aspiration tube 231 to the discharge port 69. Then, the surgeon operates the drive device 200. Accordingly, rotation of the rotation drive shaft 221 and aspiration of the aspiration tube 231 are started. The rotation drive shaft 221 rotates the rotary input unit 110. Accordingly, the proximal shaft 90 fixed to the rotary input unit 110 rotates, and the connection unit 100, the drive shaft 20, and the cutting unit 40 rotate together with the proximal shaft 90. The rotating cutting unit 40 cuts the lesion in the blood vessel.

The aspiration tube 231 applies a negative pressure to the second internal space 66 via the discharge port 69. Thus, the negative pressure is applied to the aspiration lumen 21 of the drive shaft 20 from the proximal opening portion 25 located in the second internal space 66. Therefore, as shown in FIG. 4, the lesion cut by the blade 41 of the cutting unit 40 becomes the debris and moves inside the cutting unit 40 toward a proximal end side. The debris is aspirated into the aspiration lumen 21 through the distal opening portion 26 of the drive shaft 20.

The aspirated debris passes through a proximal end of the drive shaft body 22, and as shown in FIGS. 2 and 3A, reaches the spiral groove 101 of the spiral distal section 105 inside the auxiliary member 23. The debris inside the spiral groove 101 is pushed toward the proximal side by receiving a force toward the proximal side from a wall surface of the rotating spiral groove 101. Thus, a part of the debris smoothly moves to the proximal side in the spiral groove 101 of the spiral distal section 105, and moves to the spiral groove 101 of the spiral proximal section 104. The part of the debris may be released directly from the proximal opening portion 25 opening to the proximal side into the second internal space 66 without passing through the spiral groove 101 of the spiral proximal section 104.

The spiral groove 101 of the spiral proximal section 104 is not covered by the auxiliary member 23. Therefore, the spiral groove 101 of the spiral proximal section 104 is not covered by the auxiliary member 23 and opens to the outside in the diameter direction. The debris moved to the spiral groove 101 of the spiral proximal section 104 moves from the spiral groove 101 to the outside of the spiral proximal section 104 in the diameter direction, and moves to the second internal space 66 surrounding the connection unit 100. The debris moved to the second internal space 66 surrounding the connection unit 100 enters the flow path of the discharge port 69 through the junction portion 72 and is released to the aspiration tube 231. In this case, the debris is smoothly released from the spiral groove 101 to the second internal space 66, and thus the debris is difficult to wind around the connection unit 100 having the spiral groove 101. Therefore, the proximal opening portion 25, which is a discharge port of the debris, and the spiral groove 101 are hardly blocked by the debris. Thus, the debris is difficult to retain in the second internal space 66, flows smoothly, and is discharged to the outside from the discharge port 69. The junction portion 72 is in the range S where the spiral groove 101 exists in the axial direction of the connection unit 100. At least a part of the junction portion 72 is located at the proximal side of the proximal opening portion 25. Therefore, the debris released from the proximal opening portion 25 and the spiral groove 101 to the second internal space 66 can be effectively moved to the discharge port 69 through the adjacent junction portion 72. Thus, the debris is difficult to retain in the second internal space 66, flows smoothly, and is discharged to the outside from the discharge port 69.

That is, the hollow central path P surrounding the central axis X is formed at the center of the connection unit 100. Therefore, the debris flowing through the aspiration lumen 21 can smoothly enter the spiral groove 101 of the connection unit 100. Accordingly, the debris is difficult to block the spiral groove 101, flows smoothly, and is discharged to the outside from the discharge port 69. The discharged debris reaches the pump 232 through the aspiration tube 231. The debris that has reached the pump 232 is then discharged to the waste liquid pack 235 as shown in FIG. 1. After the lesion is cut and the debris is aspirated, the surgeon stops the operation of the drive device 200. Accordingly, the drive shaft 20 stops rotating and the pump 232 stops aspirating. Accordingly, the cutting performed by the cutting unit 40 and discharging of the debris are stopped. Then, the medical device 10 is removed from the blood vessel, and the operation is completed As described above, the medical device 10 according to the first embodiment removes an object in a biological lumen. The medical device 10 includes: the rotatable drive shaft 20 which has a lumen; the cutting unit 40 which is fixed to the distal section of the drive shaft 20 and cuts the object; the rotatable proximal shaft 90 which is disposed at the proximal side of the drive shaft 20; the connection unit 100 which connects the proximal shaft 90 and the drive shaft 20 and is capable of transmitting the rotary force of the proximal shaft to the drive shaft 20; and the housing 60 which rotatably accommodates the connection unit 100 and includes the discharge port 69 for discharging the cut object to the outside, in which the drive shaft 20 has, on the proximal end face 27, the proximal opening portion 25 which opens in the axial direction along the central axis X and through which the cut object is released, and the cross-sectional shape of the connection unit 100 at a plane where the proximal end face 27 is located is different from the shape of the proximal end face 27. At least a part of the object released from the proximal opening portion 25 is released directly into an internal space of the housing 60 while moving in the axial direction without passing through the inside of the connection unit 100.

In the medical device 10 configured as described above, since the debris, which is an object formed by cutting by the cutting unit 40, and flowing to the proximal side through the lumen of the drive shaft 20, is discharged through the proximal opening portion 25 opening in the axial direction, it is difficult for the debris to wind around the rotating connection unit 100. In particular, when the opening portion (i.e., the discharge port) at the proximal side of the drive shaft 20, which is a tube body, is a side hole penetrating a side wall surface of the tube body, it is easy for the debris released from the side hole to wind around the rotating drive shaft. Compared with this case, the medical device 10 can significantly reduce the winding of the debris. Therefore, even if the debris winds around the connection unit 100, it is difficult for the debris winding due to the rotation to block the proximal opening portion 25 opening in the axial direction. That is, even if the proximal opening portion 25 opening in the axial direction is wound by the debris, since a gap is easily formed in the axial direction, the opening portion at the proximal side of the drive shaft 20 is prevented from being completely blocked by the debris. Therefore, the medical device 10 is capable of aspirating the debris formed by cutting the lesion to prevent the debris from being retained in the device 10, and effectively discharging the debris. Since the connection unit 100 has a shape different from that of the proximal section of the drive shaft 20, it is easy to form a shape that connects the proximal shaft 90 and the drive shaft 20 and does not hinder the discharge of the debris from the proximal opening portion 25. That is, since the connection unit 100 can be freely designed without depending on a shape of the drive shaft 20, the shape can be suitable for the release of the debris from the proximal opening portion 25.

The connection unit 100 is not cylindrical as a whole. Therefore, even though the connection unit 100 is connected to the tubular drive shaft 20 having the proximal opening portion 25, a state in which the proximal opening portion 25 opens in the axial direction is easily maintained. Since the connection unit 100 does not include an internal space surrounded by a cylindrical shape, the object released from the proximal opening portion 25 in the axial direction is easy to be released directly into the internal space of the housing 60.

The connection unit 100 abuts on the proximal end face 27 of the drive shaft 20. Accordingly, the connection unit 100 can be connected to the drive shaft 20 without entering the lumen of the drive shaft 20. Thus, the wide lumen of the drive shaft 20 can be allocated. Therefore, it is easy to release the debris well from the lumen of the drive shaft 20. When the drive shaft 20 does not include the auxiliary member 23, the proximal end face of the drive shaft 20 may be the proximal end face 28 of the drive shaft body 22.

The connection unit 100 has the spiral groove 101 extending spirally on the outer peripheral surface. Accordingly, the spiral groove 101 of the rotating connection unit 100 can apply a force toward the proximal side on the internal debris to assist the movement of the debris toward the proximal side. Accordingly, the debris moves along the spiral groove 101 and receives a force from the spiral groove 101 to promote the release. Therefore, it is difficult for the debris to wind around the rotating connection unit 100. Thus, the medical device 10 is capable of preventing the debris from being retained in the proximal opening portion 25 by the spiral groove 101, and effectively discharging the debris. The connection unit 100 having the spiral groove 101 extending spirally on the outer peripheral surface may be formed by twisting, for example, a substantially plate-shaped member.

One spiral groove 101 exists, and the depth H (see FIG. 3C) of the spiral groove 101 in a direction from the outer peripheral surface of the connection unit 100 toward the central axis X of the connection unit 100 may exceed the distance R from the outer peripheral surface to the central axis X of the connection unit 100. Accordingly, unlike a case where the connection unit 100 has two or more spiral grooves 101, the hollow central path P extending linearly along the central axis X is formed. Thus, the connection unit 100 can allocate a wide continuous flow path from the lumen of the drive shaft 20 while assisting the movement of the debris toward the proximal side by the spiral grooves 101. Therefore, the debris can smoothly flow through the spiral grooves 101 of the connection unit 100 without blocking the spiral grooves 101. Thus, it is easy to release the debris well from the lumen of the drive shaft 20 and the spiral grooves 101 of the connection unit 100.

The drive shaft 20 includes the drive shaft body 22 extending from the cutting unit 40 to the proximal side, and the tubular auxiliary member 23 surrounding the outer peripheral surface of the proximal section of the drive shaft body 22 and the distal section of the connection unit 100. Accordingly, a fixing force of the connection unit 100 to the drive shaft body 22 can be improved. Since the auxiliary member 23 is disposed so as to surround the drive shaft body 22 and the connection unit 100, a wide flow path through which the debris flows can be allocated. Therefore, it is easy to release the debris well from the lumen of the drive shaft 20.

A part of the connection unit 100 is inserted inside the drive shaft 20, and in the axis orthogonal cross section (i.e., the cross section orthogonal to the central axis X) at the portion where the connection unit 100 of the drive shaft 20 is inserted, an area of a flow path of the drive shaft 20 is equal to or larger than an area occupied by the connection unit 100. Accordingly, the movement of the debris flowing through the lumen of the drive shaft 20 is difficult to be obstructed by the connection unit 100 disposed inside the drive shaft 20. Therefore, the debris is difficult to be retained in the aspiration lumen 21 and is easy to be released well. The area of the flow path of the drive shaft 20 may be smaller than the area occupied by the connection unit 100.

Second Embodiment

Figure 5A:
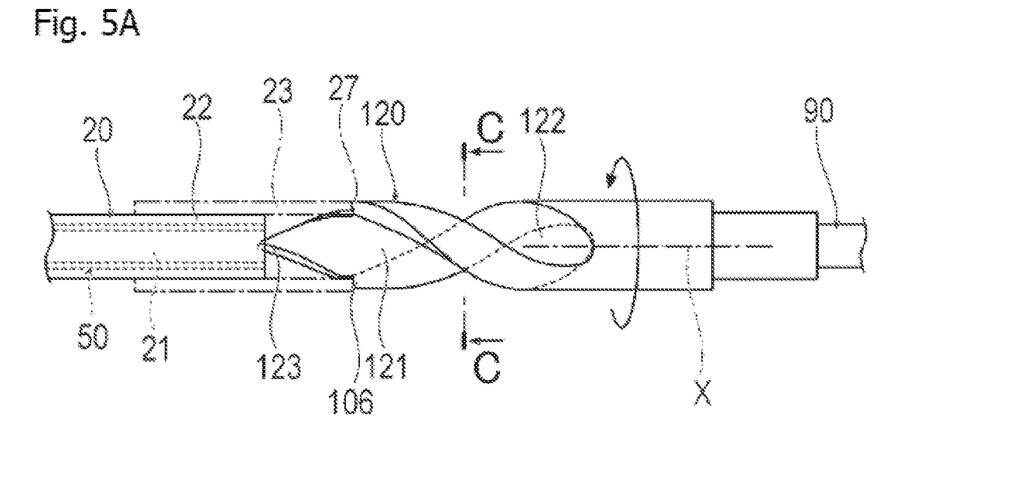
FIG. 5A is a diagram showing a partially transparent view of the vicinity of a connection unit of a medical device according to a second embodiment.
Figure 5B:
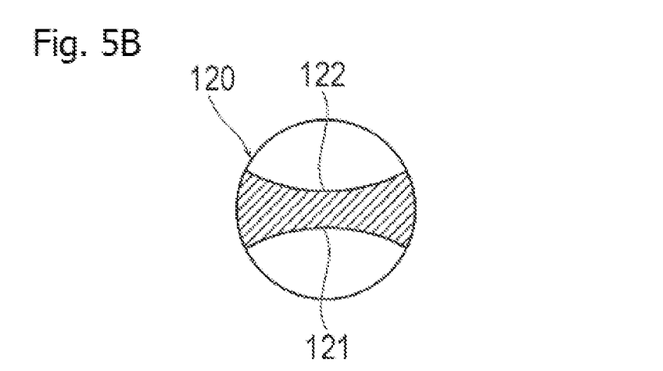
FIG. 5B is a cross-sectional view taken along a line C-C of FIG. 5A.

As shown in FIGS. 5A and 5B, the medical device 10 according to a second embodiment differs from the medical device 10 according to the first embodiment in a configuration of a connection unit 120. Parts having the same functions as those in the first embodiment are denoted by the same reference numerals, and descriptions thereof are omitted.

The connection unit 120 has two spiral grooves 121 and 122. Therefore, a portion where the spiral grooves 121 and 122 of the connection unit 120 are formed is a twisted plate shape. A distal section of the connection unit 120 disposed inside the auxiliary member 23 includes a protruding portion 123 whose outer diameter gradually decreases toward a distal side on a central axis X of the connection unit 120. That is, the connection unit 120 includes, at the distal section, the protruding portion 123 which protrudes toward a distal side and becomes thinner. Accordingly, a material constituting the connection unit 120 is reduced toward the distal side, and inevitably, a wide path through which the debris can pass is allocated. Therefore, the debris flowing to a proximal side through the lumen of the drive shaft 20 easily passes through the protruding portion 123. Thus, the debris is difficult to wind around the rotating protruding portion 123. Therefore, the medical device 10 is capable of preventing the debris formed by cutting the lesion from being retained, and effectively discharging the debris. The most distal end of the protruding portion 123 may or may not enter the aspiration lumen 21 of the drive shaft 20.

The distal section of the connection unit 120 is a substantial plate shape, and two surfaces (i.e., bottom surfaces of the spiral grooves 121 and 122) in a plate thickness direction of the connection unit 120 are disposed along the central axis X of the drive shaft 20. Accordingly, the debris flowing to the proximal side through the lumen of the drive shaft 20 flows along a surface of the rotating plate-shaped connection unit 120, so that the debris is difficult to wind around the connection unit 120.

Third Embodiment

Figure 6:
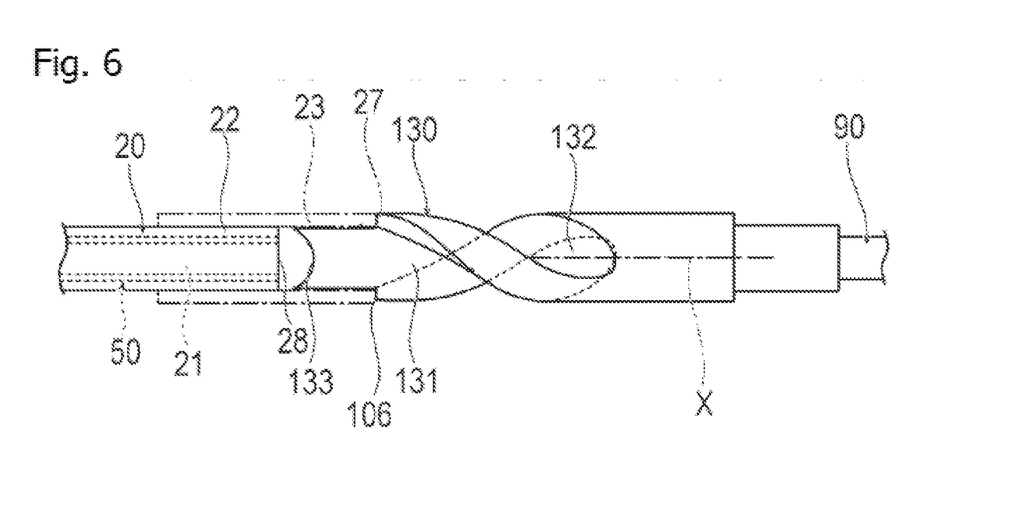
FIG. 6 is a plan view showing a partially transparent view of the vicinity of a connection unit of a medical device according to a third embodiment.

As shown in FIG. 6, the medical device 10 according to a third embodiment differs from the first embodiment in a configuration of a connection unit 130. Parts having the same functions as those in the first embodiment are denoted by the same reference numerals, and descriptions thereof are omitted.

The connection unit 130, similar to the connection unit 120 in the second embodiment, has two spiral grooves 131 and 132. A distal section of the connection unit 130 disposed inside the auxiliary member 23 includes a recessed portion 133 recessed toward a proximal side. The connection unit 130 has the recessed portion 133 that is recessed toward the proximal side on a central axis X of the connection unit 130. Accordingly, a material constituting the connection unit 130 is reduced toward a distal side, and inevitably, a wide path through which the debris can pass is allocated. Therefore, the debris flowing to the proximal side through the lumen of the drive shaft 20 easily passes through the recessed portion 133. Thus, the debris is difficult to wind around the rotating recessed portion 133. Therefore, the medical device 10 is capable of preventing the debris formed by cutting the lesion from being retained, and effectively discharging the debris. The most distal end of the connection unit 130 may or may not be in contact with the proximal end face 28 of the drive shaft body 22.

Figure 7A:
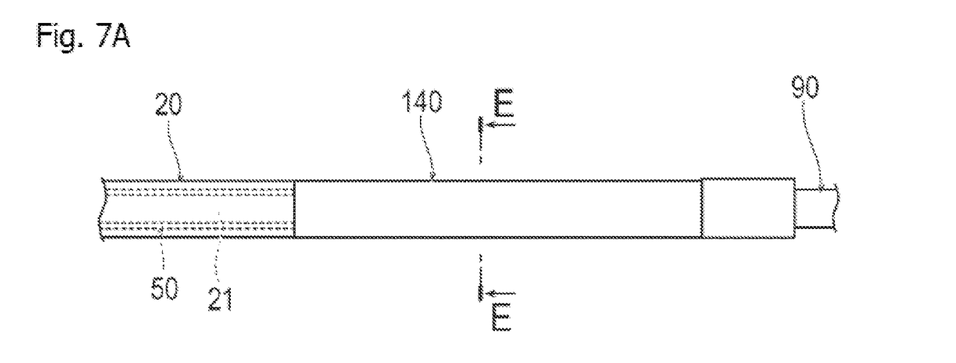
FIG. 7A is a diagram showing a connection unit according to a modification.
Figure 7B:
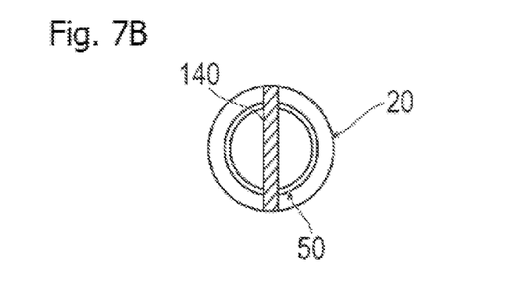
FIG. 7B is a cross-sectional view taken along a line E-E of FIG. 7A.
Figure 8A:
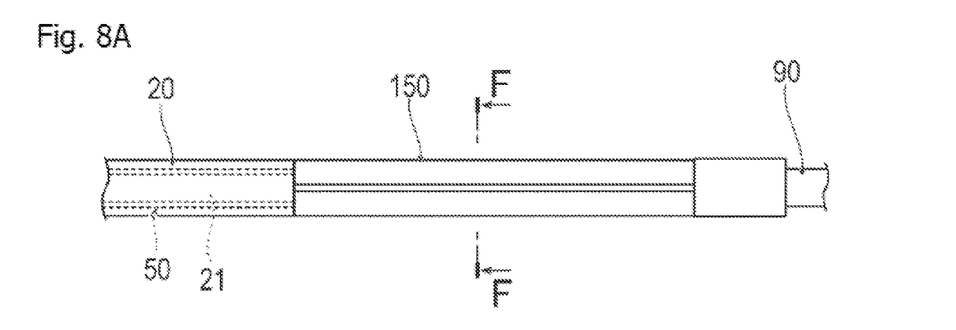
FIG. 8A is a diagram showing a connection unit according to another modification.
Figure 8B:
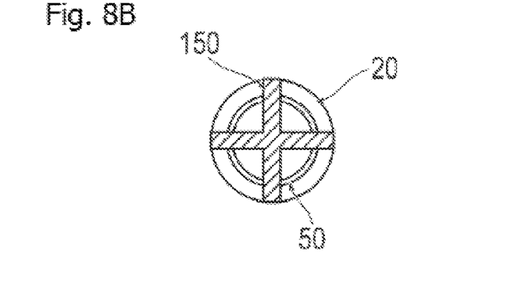
FIG. 8B is a cross-sectional view taken along a line F-F of FIG. 8A.

The invention is not limited to the embodiments described above, and various modifications could have been made by a person skilled in the art within a scope of a technical idea of the invention. For example, the biological lumen into which the medical device 10 is inserted is not limited to the blood vessel, and may be, for example, a vessel, a urinary duct, a bile duct, a fallopian tube, or a hepatic duct. The drive device 200 may be integrated with the medical device 10. As in a modification shown in FIGS. 7A and 7B, a connection unit 140 may be a flat plate shape. As in a modification shown in FIGS. 8A and 8B, a connection unit 150 may be a member having a cross-shaped axis orthogonal cross section. That is, the connection unit 150 has a plurality of plate shapes.

Each of the connection units 100-150 may be a member formed into a cylindrical shape by spirally winding one or more wire rods. The wire rod may be solid or hollow. The cutting unit 40 may or may not be provided. The object moving on the drive shaft 20 may be cut by the rotation of the connection units 100-150.

An aspiration force may be generated by the drive shaft 20 or the connection units 100-150 instead of the aspiration unit 230 connected to the discharge port 69. The drive shaft 20 and/or connection units 100-150 can generate the aspiration force by rotating if the drive shaft 20 and/or connection units 100-150 has a configuration of an Archimedes' screw pump. In this case, even though the discharge port 69 is not connected to the aspiration unit 230 generating the aspiration force, the discharge port 69 can discharge the debris.

What is claimed is:

1. A medical device that removes an object from a biological lumen, the medical device comprising:
   a rotatable drive shaft having a lumen through which the object passes;
   a cutting unit disposed at a distal end of the drive shaft and by which the object is cut;
   a proximal shaft to be rotated by a rotary force;
   a connection unit connecting the proximal shaft and the drive shaft and by which the rotary force is transmitted from the proximal shaft to the drive shaft; and
   a housing that houses the connection unit and includes a discharge port communicating with the lumen via the connection unit and through which the cut object is discharged, wherein
   the connection unit includes a first surface that faces a proximal end of the drive shaft and prevents the object that has passed through the lumen and is to be discharged through the discharge port from being retained in the connection unit along a rotation axis thereof,
   the connection unit includes a lumen extending along the rotation axis, and the lumen of the drive shaft communicates with the lumen of the connection unit, and
   a cross section of the connection unit has a crescent shape.

2. The medical device according to claim 1, wherein the first surface of the connection unit is inclined with respect to the rotation axis thereof.

3. The medical device according to claim 1, wherein the proximal end of the drive shaft partially contacts a distal end of the connection unit along the rotation axis thereof.

4. The medical device according to claim 1, wherein the connection unit has a spiral groove including the first surface and extending spirally along the rotation axis of the connection unit.

5. The medical device according to claim 4, wherein in a direction perpendicular to the rotation axis of the connection unit, a depth of the spiral groove exceeds a distance from an outer peripheral surface of the connection unit to the rotation axis thereof.

6. The medical device according to claim 1, wherein
   the connection unit has a plate including two surfaces that face each other in a plate thickness direction and extend along the rotation axis of the connection unit, and
   the first surface connects the two surfaces of the connection unit therebetween.

7. The medical device according to claim 1, wherein
   the connection unit includes a proximal section connected to the proximal shaft and a distal section connected to the drive shaft, and
   a diameter of the distal section is smaller at a position farther from the proximal section.

8. The medical device according to claim 1, wherein a distal end of the connection unit has a recessed portion recessed toward a proximal end of the connection unit.

9. The medical device according to claim 1, wherein
   the connection unit includes an inner surface that surrounds the lumen of the connection unit such that a normal line to the inner surface crosses the rotation axis of the connection unit.

10. The medical device according to claim 1, wherein
    a part of the connection unit has a cylindrical shape, and
    a part of the connection unit has the same diameter as the proximal end of the drive shaft.

11. The medical device according to claim 1, wherein the proximal end of the drive shaft is ring-shaped.

* * * * *